United States Patent

Ishii et al.

Patent Number: 5,830,414
Date of Patent: Nov. 3, 1998

[54] AIR CLEANING FILTER

[75] Inventors: Tsutomu Ishii, Tokyo; Seiichi Takizawa, Sagamihara; Tetsuo Shimamura, Osaka; Michinori Hashimoto, Tokyo; Shozo Ichimura, Tokyo; Fumio Karibe, Tokyo, all of Japan

[73] Assignees: Kondoh Industries Limited; Cambridge Filter Japan, Ltd., both of Tokyo; Unitika Ltd., Amagasaki; Nippon Chemical Industrial Co., Ltd., Tokyo, all of Japan

[21] Appl. No.: 682,569
[22] PCT Filed: Nov. 30, 1994
[86] PCT No.: PCT/JP94/02016
§ 371 Date: Jul. 29, 1996
§ 102(e) Date: Jul. 29, 1996
[87] PCT Pub. No.: WO96/16719
PCT Pub. Date: Jun. 6, 1996
[51] Int. Cl.$^6$ .............................................. A62B 7/08
[52] U.S. Cl. .......................... 422/122; 55/524; 55/527; 422/120
[58] Field of Search ........................... 422/5, 120, 122; 55/522, 524, 527; 96/108

[56] References Cited

U.S. PATENT DOCUMENTS

| 4,200,609 | 4/1980 | Byrd ........................................ 422/122 |
| 5,124,856 | 6/1992 | Brown et al. ........................ 360/97.03 |
| 5,302,354 | 4/1994 | Watvedt et al. ....................... 422/177 |
| 5,344,626 | 9/1994 | Abler ....................................... 423/210 |
| 5,607,647 | 3/1997 | Kinkead ................................. 422/122 |
| 5,626,820 | 5/1997 | Kinkead et al. ....................... 422/122 |

*Primary Examiner*—Krisanne Thornton
*Attorney, Agent, or Firm*—Oblon, Spivak, McClelland, Maier & Neustadt, P.C.

[57] ABSTRACT

An air cleaning filter having a carrier made of activated carbon fibers in the form of a web which supports at least one kind of chemical agent selected from the group consisting of (a) an alkali agent selected from a hydroxide or carbonate or an alkali metal, (b) an acidifying agent selected from acid aluminum phosphate or phosphoric acid, and (c) an oxidizing agent composed of two compounds, i.e. active manganese dioxide resulting from an alkali permanganate and an alkali iodate, or which supports combined chemicals of (a) the alkali agent and (c) the oxidizing agent, or combined chemicals of (b) the acidifying agent and (c) the oxidizing agent, wherein one or both surfaces of the web are covered with a nonwoven fabric to make an integrated filter.

10 Claims, 1 Drawing Sheet

AIR CLEANING FILTER

TECHNICAL FIELD

The present invention relates to a high performance air cleaning filter which can effectively clean contaminated environmental air containing very low concentrations of pollutants.

BACKGROUND ART

In the present state where cleaning of the earth's environment has been a big problem, the control and prevention of air pollution in particular has been an urgent matter to be solved, and the cleaning of air which contains low concentrations of pollutants has been strongly demanded in every environment including working environments in various industries and living environments.

Conventionally, although dry processes and wet processes have been known for cleaning air, a dry process employing activated carbon has been practically used for a long time due to its simplicity. Also various air cleaning agents which exhibit selective adsorption capabilities according to the kinds of polluting gases have been developed; for example, a porous carrier supporting a base or an acid chemical is regarded as effective for removing an acid or a basic gas. Particularly, an air cleaning agent comprising a carrier supporting an oxidizing agent or a reducing agent has been widely used in industry since it has such a cleaning capacity that the polluting gas is decomposed by the strong oxidizing/reducing power.

Among such air cleaning agents are an agent comprising a carrier such as activated alumina or zeolite, supporting potassium permanganate (Japanese Patent Laid-Open Nos. 60-827,3-23863 and the like), an agent comprising an activated carbon supporting an iodate and/or an inorganic acid (Japanese Patent Laid-Open Nos. 61-68136, 62-161372, and 62-161373) and the like.

Also an air cleaning agent which comprises an activated carbon honeycomb supporting iodine and inorganic iodide has been known (EP-052077A1).

An air cleaning agent which comprises activated carbon fibers supporting a MnO type chemical agent and which removes the bad smell of aldehydes and the like is also known (Japanese Patent Laid-Open No.3-288545).

These air cleaning agents have been brought into actual use according to applications, but each agent has its own merits and demerits, and there are problems that the uses may be limited due to the inherent physical properties of each agent. For example, an air cleaning agent of potassium permanganate type is a soluble and strong oxidizing agent, thus is highly dangerous requiring great caution in its handling. Accordingly, it cannot be used in consumer products for ordinary household environments. Though the activated carbon is very safe during use, since the removal mechanism is based on physical adsorption, the degree of polluting gas removal is naturally restrained. Further, when saturated, it loses the adsorption activity and even exhibits desorption phenomenon. Accordingly, in most cases, the activated carbon is used by supporting a chemical agent, but still it cannot be expected to have a long working life and a high capacity for removing the polluting gas of a low concentration.

PROBLEMS TO BE SOLVED BY THE INVENTION

Recently, for the purpose of improving the product precision and the yields in the production of precision electronics including semiconductors, or for the purpose of allowing permanent storage of high-quality art such as paintings without causing discoloration, it has been eagerly desired to develop an air cleaning agent which is safe, easy to handle and can remove polluting gas of a low concentrations completely and easily.

The present invention has been developed as a result of an intensive study in view of the above-mentioned demand, and it is aimed at providing an air cleaning filter which is safe, has a long working life, a sufficient capacity for removing a polluting gas of low concentrations, and which has such a structure that it can be easily installed.

DISCLOSURE OF THE INVENTION

To achieve the above-mentioned objects the air cleaning filter of the present invention comprises a carrier made of activated carbon fibers in the form of a web which supports one kind of chemical agent selected from the group consisting of (a) an alkali agent selected from a hydroxide or carbonate of an alkali metal, (b) an acidifying agent selected from acid aluminium phosphate or phosphoric acid, and (c) an oxidizing agent composed of two compounds, i.e. activated manganese dioxide resulting from an alkali permanganate and an alkali iodate, or which supports combined chemicals of (a) the alkali agent and (c) the oxidizing agent, or combined chemicals of (b) the acidifying agent and (c) the oxidizing agent, wherein one or both surfaces of the web are covered with a nonwoven fabric to make an integrated filter.

BRIEF DESCRIPTION OF THE DRAWINGS

In FIG. 1, the reference numerals designate the following. 1: an air cleaning filter, 2: a supporting frame, 3: a spacing, 4: a sealing material, and 5: a gasket.

In FIG. 2, 1a designates a nonwoven fabric and 1b designates a web of activated carbon fibers.

BEST MODE FOR CARRYING OUT THE INVENTION

Figure 1:
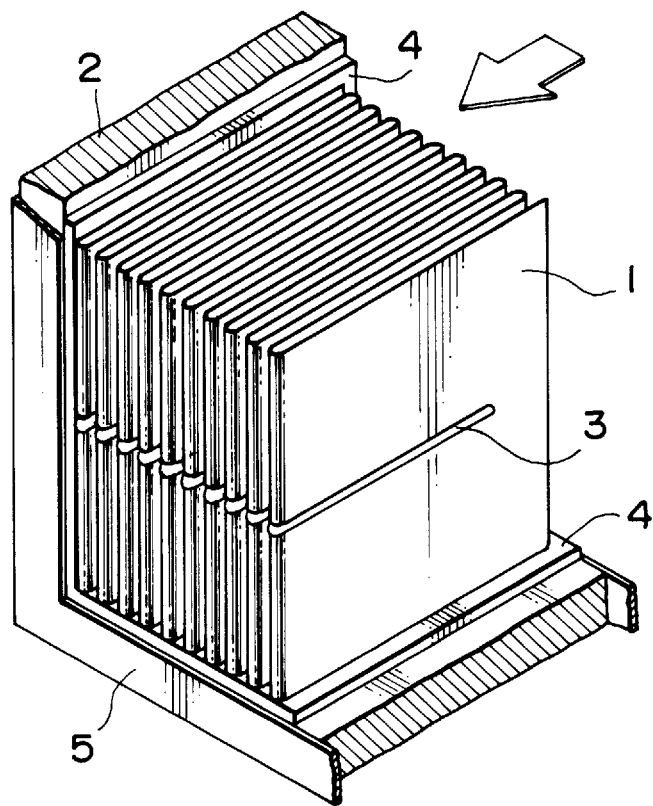
FIG. 1 illustrates a perspective cutaway view of one example of an air cleaning apparatus wherein an air cleaning filter of the present invention is used.

The carrier used for the air cleaning filter according to the present invention comprises activated carbon fibers which are made into the form of a web. Althogh the thickness of the web depends on use, generally it is from 0.5 to 15 mm and preferably in a range of 1 to 10 mm. This is because when the thickness of the web is beyond the above-mentioned range, it is difficult to form a uniform web or the moldability of the web becomes inferior, thus becoming less practical.

The shape and size (area) of the web depend on the use and on the design of the housing for accommodating the web. Thus they are not particularly limited.

The activated carbon fiber has a very large specific surface area, usually having a BET specific surface area of 800 to 1400 $m^2/g$, and a large pore volume. And above all, it has a very light weight, thus it is specially important as a carrier according to the present invention, and the production history thereof is not particularly limited.

Among such products are those obtained by carbonization and activation of a thermosetting resin such as a phenol resin, urea resin, and epoxy resin, tar pitch, and a fiber such as polyacrylonitrile and rayon. According to the present invention, these commercially available products can be suitably used.

If necessary, a natural fiber such as a cellulose fiber and wool fiber, an inorganic or organic synthesized fiber such as a glass fiber, slag wool, polyester, polyamide, rayon, and polyacrylonitrile can be used together.

The chemical agent to be supported on the above-mentioned activated carbon fiber carrier is an agent which can remove the polluting gas in an atmospheric environment by neutralization or oxidation, and is either (a) an alkali agent, (b) an acidifying agent or (c) an oxidizing agent. An example of (a) an alkali agent may be selected from a hydroxide or a carbonate of an alkali metal such as Li, Na and K, an example of (b) an acidifying agent may be selected from an acid aluminium phosphate or phosphoric acid, but the use of the acid aluminium phosphate is most practical. An example of (c) an oxidizing agent is an agent which is composed of an iodate and active manganese dioxide resulting from an alkali permanganate. Particularly preferable is a mixed oxidizing agent comprising potassium iodate and manganese dioxide resulting from potassium permanganate.

Such chemical agent can be used alone or in admixture of two or more kinds, i.e. in combination of (a) and (c), or in combination of (b) and (c), according to the conditions of air pollution and the purpose of the cleaning.

With these chemical agents, if necessary, other chemical agents including a reducing agent such as an alkali phosphite and an alkali hypophosphite, or an antibacterial agent can be suitably used as well.

An example of the antibacterial agent includes silver nitrate, a quaternary ammonium salt such as an alkyldimethylbenzylammonium chloride and didecyldimethylammonium chloride, a phosphonium salt such as triethyloctadecylphosphonium chloride and a tetraalkylphosphonium chloride, a vinylbenzyltrialkylphosphonium chloride or a polymer thereof, dihydroacetic acid or an alkali metal thereof, sorbic acid or an alkali metal salt thereof. Such agent can be used alone or in admixture of two or more kinds.

The amount of the above-mentioned chemical agent supported depends on the kind of the chemical agent, the physical property of the carrier and the use of the air cleaning agent. However, it is set in a range of 0.1 to 50% by weight, preferably in a range of 0.2 to 30% by weight, of the total weight of the activated carbon fiber carrier and the chemical agent. This is because, when it is less than 0.1% by weight, since the amount of the chemical agent supported is small, the removal of the polluting gas is mainly determined by the physical adsorption of the activated carbon, and the removal capacity becomes low or the removal capacity quickly decreases; on the other hand, when the amount is equal to or more than 50% by weight, the removal capacity is not improved in proportion to the increase in the amount of the agent supported. Further, as the agent closes the micro pores of the activated carbon, the removal capacity is decreased rather than increased.

Among the above-mentioned chemical agents, particularly preferable is an oxidizing agent comprising potassium iodate and active manganese dioxide resulting from a permanganate of an alkali metal, since it has a good capacity for removing a low concentration polluting gas, even if it is supported in a small amount, and it can be handled safely. For example, when a chemical agent solution of potassium permanganate is supported on a carrier, it is converted into active manganese dioxide by the redox reaction with the activated carbon and eventually supported as an insoluble, powerful and safe oxidizing agent. Active manganese dioxide, to which a small amount of particulates of a metal such as copper, silver, palladium and platinum or a compound of such metal is added if necessary, is preferable due to its enhanced oxidation activity.

When a chemical agent is supported on the above-mentioned activated carbon fiber, the following practically insoluble inorganic particulates may be supported as well, if desired. Examples of such particulates include an oxide, hydroxide, silicate or phosphate of calcium, magnesium, aluminium, iron, zinc, titanium, zirconium and copper, granular activated carbon, and aluminosilicate (zeolite). Such particulates can be used alone or in admixtures of two or more kinds. These components can be either natural or synthetic, however, they are desirably as porous and impalpable as possible. The substantially insoluble powder inorganic carrier should be selected according to the use of the air cleaning agent and the filter, and the amount of the powder blended is not particularly limited. However, it is preferable to be at most 30% by weight of the total weight of the carrier.

These particulates are used if necessary as described above, and this is because their use may widen the polluting gas removal spectrum in the case of the combined air pollution, or it may increase the capacity of the chemical agent supported on the activated carbon fiber for removing the polluting gas, or extend the use life of the agent.

The above-mentioned chemical agent is either supported on an activated carbon fiber carrier which was previously molded into the form of a web, or supported on an activated carbon first and then molded into the form of a web. The process by which the above-mentioned chemical agent is supported on the activated carbon fiber carrier can be any process as long as the chemical agent can be supported uniformly on the carrier; for example, a process wherein the carrier is immersed in an aqueous solution of the chemical agent, a process wherein the carrier and the chemical agent are directly mixed by using an appropriate mixer, or by spray mixing and the like are practical. In the former example employing the adsorption supporting process, the activated carbon fiber is immersed in a solution of a chemical agent from room temperature to 40° C. for 1–10 minutes. Then an extra solution of the chemical agent adhered on the surface is removed by centrifugation, then it is dried if necessary, and molded into the form of a web to give a web form body. It is also possible to make the fibrous material into a web form and immerse it in the solution of the chemical agent or subject it to spraying treatment of the solution. The inorganic powder can be supported on the fibrous material either directly or by mixing the inorganic powder in the solution of each chemical agent which is then used for treating the fibrous material.

In addition, when a chemical agent is supported on the activated carbon fiber carrier, an assistant component or an appropriate binding agent, and an auxiliary component such as a water soluble polymer including MC, CMC and soda alginate, and silica sol, can be used together if necessary.

One of the features of the air cleaning filter according to the present invention is the integrated form wherein the surface of the above-mentioned activated carbon fiber web supporting the chemical agent is covered with a nonwoven fabric.

The nonwoven fabric is known in the field and refers to a fiber aggregate which is not treated by spinning, weaving or braiding, but subjected to treatment by chemical means or mechanical and chemical action or treatment in the presence of an appropriate water and heat, thereby bonding the fibers to each other. Usually it is made of a fiber aggregate in the form of a web or a sheet as a base, which is bonded with an adhesive to strengthen the adhesion among fibers or the adhesion among fibers is strengthened by the use of thermoplastic resin fibers.

The material thereof is not particularly limited, and those made from a mixture of rayon, cotton, and a synthesized fiber, or those made from a synthesized fiber such as cellulose fiber, polyamide, polyester, polyester/polyethylene, polypropylene, polypropylene/polyethylene are mainly employed. The thickness of the nonwoven fabric is not particularly specified. However, it is normally from 1.5 to 8.0 mm and preferably from 2 to 5 mm.

The integrated form made by using such a nonwoven fabric refers to a form of an integrated filter wherein at least one side of a web of the activated carbon fiber supporting the chemical agent is covered with the nonwoven fabric and they are made into one body. Accordingly, it includes a case wherein both the upper and the lower surfaces of the activated carbon fiber web are held between nonwoven fabrics or a case wherein the activated carbon fiber web is wrapped in a bag made of a sheet-like nonwoven fabric to make an integrated sheet like body. The thickness and size of the sheet like body are not particularly limited. However, the thickness is usually 2 to 25 mm and preferably 3 to 20 mm.

Figure 2:
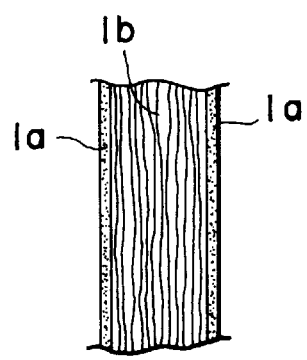
FIG. 2 illustrates an enlarged sectional view of one example of an air cleaning filter of the present invention.

FIG. 2 illustrates an enlarged view of a cross section of one example of an air cleaning filter of the present invention. In FIG. 2, activated carbon fiber web $1b$ supports an air cleaning agent selected from the above-mentioned components (a), (b) and (c), and both surfaces are coated with nonwoven fabric $1a$ to protect the activated carbon fiber web, to increase the mechanical strength, and at the same time to improve the capacity for removing particulates contained in air.

As for the integration of the activated carbon fiber and the nonwoven fabric, the activated carbon fiber and the nonwoven fabric need not be adhered beforehand, if they can be anchored from outside. They can also be physically anchored in a desired system using an anchoring point.

When a sheet like body in which an activated carbon fiber supporting a chemical agent and a nonwoven fabric are integrated, is used as an air cleaning filter, in most cases it is in a range of 50 to 800 g/m$^2$, preferably 100 to 500 g/m$^2$, though there are variety of selections according to the use, the kind of the chemical agent, the thickness of the activated carbon fiber sheet and the kind and the thickness of the nonwoven fabric.

The air cleaning filter according to the present invention can contain water in an amount of more than the equilibrium water content as far as consolidation or deterioration of the filter does not occur during storing, transportation or handling, and it is rather preferable for the filter to contain 5–15% by weight of water based on the total weight. The water content in this case refers to all the components lost in weight after the air cleaning filter is dried at 100° C. for 1 hour, and the amount refers to a ratio based on the air cleaning filter.

For shaping an air cleaning filter into an air cleaning apparatus or unit, a belt-shaped air cleaning filter is folded alternately at regular intervals to produce a continuous or semicontinuous fanfold body, or air cleaning filters are laminated in the form of a panel. The air cleaning filter may also be molded into the form of a honeycomb, which is then laminated or wound to form an air cleaning apparatus. Such an air cleaning apparatus can be naturally used as a single unit, but in many cases, plural units are combined and used in the form of a composite unit according to the volume of the air to be treated. In such a case, the filter in each unit is not limited to contain an air cleaning agent of the same chemical agent, but air cleaning filters supporting different chemical agents can be combined to make up an air cleaning apparatus according to the purpose of cleaning, and the condition of the combined pollution.

FIG. 1 illustrates a perspective cutaway view of one mode of an air cleaning apparatus according to the present invention, wherein 1 designates an air cleaning filter, and 2 designates a supporting frame. The air cleaning filter 1 is formed into a continuous fanfold body by folding a belt-shaped sheet like body alternately so that each fold has the same width and the neighbouring folds have the same gap between them. This is secured inside of the supporting frame 2 which is made of a molded plate of aluminium or a synthesized resin and the like. For securing the air cleaning filter 1, a spacing 3 is used and the part which is in contact with the inner surface of the supporting frame 2 is tightly sealed with a sealant 4 such as a resin type adhesive, in order to prevent the short passage of air passing through the apparatus. At the top of the supporting frame 2, a gasket 5 to which an elastic material such as rubber is bonded is placed to prevent the leaking of the air when plural units are combined. The air to be treated comes from the direction shown by the arrow, passes through the filter system and is cleaned.

The apparatus employing the air cleaning filter according to the present invention has little loss of pressure by permeation of air and is very light in weight. Thus in order to carry out effective cleaning of air, it can be designed in the form of a unit wherein air cleaning agents of the same kind or different kinds are combined according to the desired purpose.

In the air cleaning filter according to the present invention, activated carbon fibers in the form of a sheet, supporting one or more kinds of chemical agents selected from the above-mentioned (a) alkali agent, (b) acidifying agent or (c) oxidizing agent is integrated with a nonwoven fabric.

Accordingly, the high adsorbing capacity of the activated carbon fiber and the chemical reaction of the chemical agent synergistically act on the polluting gas in the atmosphere and provides an excellent air cleaning capacity. Besides, since the nonwoven fabric and the carbon fiber webs are formed into an integral filter, not only the scattering of particulates of the supported chemical agent caused by the air passing through the filter can be cut, but also the particulates in the atmosphere can be cut down.

In particular, because of the above-mentioned structure, the air cleaning filter according to the present invention exhibits much less pressure loss from the permeation of air, and is light in weight compared with those of granular type, thus an air cleaning apparatus can be designed more functionally by laminating filters supporting the same kind of or different kinds of chemical agents in the housing.

The air cleaning filter according to the present invention and the air cleaning apparatus employing the air cleaning filter of the present invention can effectively remove single or combined poisonous polluting gasses of various kinds. The objects to be removed include, for example, hydride gases such as hydrogen sulfide, phosphine, arsine, germane, silane, ozone, CO, NOx, SOx, amines, mercaptans, carbonyl sulfide, aldehydes, phenols, and unsaturated hydrocarbons such as ethylene or bad smells such as from sewage, animals, or excrement and urine that are contaminated with these components. In addition, the air cleaning filter and the air cleaning apparatus utilizing the filter have bactericidal activity due to the strong oxidizing power of the filter, and particularly those which support copper, silver, or ions thereof and other antibacterial agents, exhibit even higher antibacterial activity. Thus noxious microorganisms in air including various bacteria, molds and viruses can be removed as well.

EXAMPLES

To further illustrate the present invention, the following Examples and Comparative examples are given.

Examples 1–3, Comparative Example 1

Active carbon fibers were immersed in a KMnO$_4$ aqueous solution (3% by weight), a mixed aqueous solution of KMnO$_4$ and KIO$_3$ (KMnO$_4$: 3% by weight, KIO$_3$: 0.3% by weight), and a mixed aqueous solution of KIO$_3$ and K$_2$CO$_3$ (KIO$_3$: 0.4% by weight, K$_2$CO$_3$: 2% by weight) respectively to support each chemical agent. They were then dehydrated by a centrifugal separator, dried, and then subjected to roll forming to be made into the form of a belt, to provide a web having a thickness of 4 mm supporting the chemical agents. The web was held between nonwoven fabrics made of nylon and rayon to prepare an air cleaning filters (Samples A–C). Then, the air cleaning filters were folded alternately at regular intervals to form a fanfold body as shown in FIG. 1, and secured onto the supporting frame of the housing to produce air cleaning apparatuses (height of 60 cm, width of 60 cm and depth of 30 cm). As a Comparative example, an air cleaning filter of activated carbon fibers supporting no chemical agent was employed (Sample D).

A part of a sheet-like body of an air cleaning filter employing $KMnO_4$ type chemical agent was cut out and leached out by water, but no reddish purple coloration due to $MnO_4^-$ was substantially recognized. This showed that the agent was converted into insoluble and active manganese dioxide and supported on the sheet-like body.

Evaluation of an air cleaning apparatus employing the air cleaning filters of Samples A–D, in regards to capacity for removing $SO_2$ gas was carried out under the following conditions.

Gas concentration at entrance: about 10–20 ppm
Gas temperature at entrance: 20°–25° C.
Gas humidity at entrance: 20–25% RH
Plane wind velocity: 0.5 m/sec
Measurement method: Gastech detector tube method The results are shown in Table 1 in comparison with the blend compositions of the air cleaning agent.

Examples 7–8

A belt-like web carrier having a thickness of 4 mm, wherein 10% by weight of zeolite based on the total weight of activated carbon fibers was mixed with the activated carbon fibers, was immersed in a chemical agent used in Example 2 so that the chemical agent was supported on the carrier which was then hydrated, dried and held between the same nonwoven fabric used in Example 1 to prepare an air cleaning filter in the form of a sheet (Sample E). Similarly, the chemical agent used in Example 2 was supported on a belt-like web carrier which had been produced by mixing cotton fibers and powder activated carbon in an amount of 20% by weight of the total weight of the cotton fibers, and an air cleaning filter was prepared (Sample F).

These air cleaning filters were used to produce air cleaning apparatuses in a manner analogous to that of Example 1. The air cleaning apparatus was subjected to a $H_2S$ gas removal capacity evaluation test under the following conditions and the results obtained are shown in Table 3. A part of a sheet of an air cleaning filter using $KMnO_4$ type chemical agent was leached out by water but no reddish purple coloration due to $MnO_4^-$ could be substantially observed. This showed that the agent was converted into active manganese dioxide and supported on the carrier.

Gas concentration at entrance: about 10 ppm
Gas temperature and humidity at entrance: 20°–21° C., 66–67% RH
Gas flow rate: 8.8 l/min
Plane wind velocity: 0.3 m/sec
Measurement method: Gastech detector tube method

TABLE 1

| | | Composition (wt %) | | | | $SO_2$ Removal rate (%) | | | | |
|---|---|---|---|---|---|---|---|---|---|---|
| | Sample | $KMnO_4$ | $KIO_3$ | $K_2CO_3$ | $H_2O$ | 5 hr | 9 hr | 15 hr | 19 hr | 23 hr |
| Example No. | | | | | | | | | | |
| 1 | A | 0.5 | — | — | 13.5 | 95.0 | 93.2 | 90.1 | 85.2 | 83.0 |
| 2 | B | 0.4 | 0.4 | — | 12.6 | 97.0 | 97.5 | 94.4 | 90.0 | 88.2 |
| 3 | C | — | 0.5 | 0.2 | 13.5 | 96.5 | 95.8 | 92.9 | 87.5 | 85.1 |
| Comparative Example No. 1 | D | — | — | — | — | 91.3 | 85.9 | 82.3 | 74.8 | 62.1 |

Example 4–6, Comparative Example 2

An evaluation of the removal capacity was carried out in a manner analogous to that of Example 1, except that the concentration of $SO_2$ gas at entrance was changed to 200 ppb, and a different length of measurement time was employed. The results are shown in Table 2.

TABLE 2

| | | Composition (wt %) | | | | $SO_2$ Removal rate (%) | | | |
|---|---|---|---|---|---|---|---|---|---|
| | Sample | $KMnO_4$ | $KIO_3$ | $K_2CO_3$ | $H_2O$ | 24 hr | 72 hr | 168 hr | 264 hr |
| Example No. | | | | | | | | | |
| 4 | A | 0.5 | — | — | 13.5 | 98.1 | 96.2 | 92.3 | 88.6 |
| 5 | B | 0.4 | 0.4 | — | 12.6 | 99.8 | 99.8 | 99.7 | 99.7 |
| 6 | C | — | 0.5 | 0.2 | 13.5 | 99.7 | 99.0 | 98.5 | 98.2 |
| Comparative Example No. 2 | D | — | — | — | — | 97.5 | 94.3 | 90.5 | 85.2 |

TABLE 3

| Example No. | Sample | Composition (wt %) | | | | $H_2S$ Removal rate (%) | | | | | |
|---|---|---|---|---|---|---|---|---|---|---|---|
| | | $KMnO_4$ | Zeolite A | $KIO_3$ | $H_2O$ | 15 min | 60 | 120 | 180 | 240 | 300 |
| 7 | E | 0.4 | 10 | 0.4 | 13.5 | 100 | 99.0 | 97.0 | 95.5 | 90.0 | 89.7 |
| 8 | F | 0.4 | 20 | 0.4 | 12.6 | 100 | 99.2 | 99.0 | 97.0 | 95.3 | 92.0 |

Examples 9–12, Comparative Examples 3–6

Active carbon fibers were immersed in an aqueous solution of potassium carbonate (34% by weight) to support the chemical agent on them. They were then dehydrated by a centrifugal separator, dried, and then molded into a belt-like web having a thickness of 4 mm. The upper and lower surfaces of the sheet-like body supporting the agent ($K_2CO_3$: about 20% by weight) were held between nonwoven fabrics made of polyester fibers, to prepare an air cleaning filter (Sample G). Then, the air cleaning filter was used for producing an air cleaning apparatus in a manner analogous to that of Example 1. The apparatus was evaluated on the capacity for removing various acid gasses under the following conditions, and the results are shown in Table 4. An analogous evaluation was carried out using activated carbon fibers employing no chemical agent (Sample D), to carry out comparison, and the results are also shown in Table 4.

Gas concentration at entrance: about 20 ppm or 250 ppb
Gas temperature at entrance: 20°–25° C.
Gas humidity at entrance: 20–25% RH
Plane wind velocity: 0.5 m/sec
Measurement method:
Gastech detector tube method (When the gas concentration at entrance was about 20 ppm)
Ion chromatograph method (When the gas concentration at entrance was 250 ppb)

chemical agent, and dehydrated by a centrifugal separator, dried, and then molded into a belt-like web having a thickness of 4 mm. The upper and lower surfaces of the sheet-like body supporting the chemical agent ($P_2O_5$: about 25% by weight) were held between nonwoven fabrics made of polyester fibers to produce an air cleaning filter (Sample H). Then, the air cleaning filter was used to prepare an air cleaning apparatus in a manner analogous to that of Example 1. The air cleaning apparatus was subjected to an evaluation of ammonia gas removal capacity under the following conditions and the results are given in Table 5. For comparison, activated carbon fibers supporting no chemical agent (Sample D) were subjected to the same evaluation process and the results are also shown in Table 5.

Gas concentration at entrance: about 20 ppm or 250 ppb

Gas temperature at entrance: 20°–25° C.

Gas humidity at entrance: 20–25% RH

Plane wind velocity: 0.5 m/sec

Measurement method:

Gastech detector tube method (When the gas concentration at entrance was about 20 ppm)

TABLE 4

| | Sample | Poluting gas | Gas inlet conc. (ppm) | Removal rate (%) | | | | | |
|---|---|---|---|---|---|---|---|---|---|
| | | | | 0.5 hr | 5 hr | 9 hr | 15 hr | 19 hr | 23 hr |
| Example No. | | | | | | | | | |
| 9 | G | HCl | 20 | 100 | 100 | 100 | 100 | 100 | 99.9 |
| 10 | G | HCl | 250 | 100 | 100 | 100 | 100 | 100 | 99.9 |
| 11 | G | HF | 20 | 100 | 100 | 100 | 100 | 100 | 100 |
| 12 | G | HF | 250 | 100 | 100 | 100 | 100 | 100 | 100 |
| Comparative Example No. | | | | | | | | | |
| 3 | D | HCl | 20 | 50 | 0 | 0 | 0 | 0 | 0 |
| 4 | D | HCl | 250 | 40 | 0 | 0 | 0 | 0 | 0 |
| 5 | D | HF | 20 | 50 | 0 | 0 | 0 | 0 | 0 |
| 6 | D | HF | 250 | 40 | 0 | 0 | 0 | 0 | 0 |

Examples 13–14, Comparative Examples 7–8

Activated carbon fibers were immersed in an aqueous phosphoric acid solution (30% by weight) to support the Ion chromatograph method (When the gas concentration at entrance was 250 ppb)

TABLE 5

|  | Sample | Poluting gas | Gas inlet conc. (ppm) | Removal rate (%) | | | | | |
|---|---|---|---|---|---|---|---|---|---|
|  |  |  |  | 0.5 hr | 5 hr | 9 hr | 15 hr | 19 hr | 23 hr |
| Example No. | | | | | | | | | |
| 13 | H | $NH_3$ | 20 | 100 | 100 | 100 | 100 | 100 | 100 |
| 14 | H | $NH_3$ | 250 | 100 | 100 | 100 | 100 | 100 | 100 |
| Comparative Example No. | | | | | | | | | |
| 7 | D | $NH_3$ | 20 | 50 | 0 | 0 | 0 | 0 | 0 |
| 8 | D | $NH_3$ | 250 | 40 | 0 | 0 | 0 | 0 | 0 |

Examples 15–17, Comparative Example 9

Air cleaning filters of Examples 1–3 were bent into a wavy form, and laminated and secured onto the supporting frame of the housing to produce an air cleaning apparatus of honeycomb laminate structure (height of 6.9 cm, width of 5.5 cm and depth of 7.0 cm). A part of a sheet of an air cleaning filter using $KMnO_4$ type chemical agent was cut out and leached into water but no reddish purple coloration due to $MnO_4^-$ was substantially recognized. This showed that the agent was converted into active and insoluble manganese dioxide and supported on the sheet-like carrier. An air cleaning filter of activated carbon fiber supporting no chemical agent was used as a Comparative example (Sample D).

The obtained samples A–D were used for producing air cleaning apparatuses and they were subjected to the evaluation of capacity for removing $SO_2$ gas under the following conditions.

Gas concentration at entrance: about 10–20 ppm
Gas temperature at entrance: 20°–25° C.
Gas humidity at entrance: 20–25% RH
Plane wind velocity: 0.5 m/sec
Measurement method: Gastech detector tube method The results are shown in Table 6 in comparison with the blend compositions of the air cleaning agents.

TABLE 6

|  | Sample | Composition (wt %) | | | | $SO_2$ Removal rate (%) | | | | |
|---|---|---|---|---|---|---|---|---|---|---|
|  |  | $KMnO_4$ | $KIO_3$ | $K_2CO_3$ | $H_2O$ | 5 hr | 9 hr | 15 hr | 19 hr | 23 hr |
| Example No. | | | | | | | | | | |
| 15 | A | 0.5 | — | — | 13.5 | 96.8 | 94.5 | 91.2 | 84.3 | 82.0 |
| 16 | B | 0.4 | 0.4 | — | 12.6 | 98.5 | 98.1 | 96.4 | 94.2 | 92.2 |
| 17 | C | — | 0.5 | 0.2 | 13.5 | 98.1 | 97.7 | 95.0 | 91.8 | 90.0 |
| Comparative Example No. 9 | D | — | — | — | — | 91.8 | 86.3 | 81.5 | 72.3 | 60.5 |

Industrial Applicability

As described above, according to the present invention, there is provided a quality air cleaning agent and air cleaning filter which exhibit excellent capacities for removing a polluting gas of a very low concentration for a long time. In addition, the air cleaning agent and the air cleaning filter of the present invention are very safe and light in weight. Thus they can be expected to be useful in various applications ranging from industrial use to general consumer use.

What is claimed is:

1. An air cleaning filter comprising an activated carbon carrier supporting a chemical agent for removing a polluting gas existing in an atmospheric environment by neutralization or oxidation and decomposition thereof, wherein the activated carbon carrier comprises activated carbon fibers in the form of a web which supports at least one kind of chemical agent selected from the group consisting of (a) an alkali agent selected from a hydroxide or carbonate of an alkali metal, (b) an acidifying agent selected from acid aluminium phosphate or phosphoric acid, and (c) an oxidizing agent composed of active manganese dioxide resulting from an alkali permanganate and an alkali iodate, or which supports combined chemicals of (a) the alkali agent and (c) the oxidizing agent, or combined chemicals of (b) the acidifying agent and (c) the oxidizing agent, wherein one or both surfaces of the web are covered with a nonwoven fabric to make an integrated filter.

2. An air cleaning filter according to claim 1, wherein the activated carbon fiber in the form of a web has a thickness in the range of 0.5 to 15 mm.

3. An air cleaning filter according to claim 1, wherein an amount of the chemical agent supported is 0.1–50% by weight of the total weight of the activated carbon fiber carrier in the form of a web and the chemical agent.

4. An air cleaning filter according to claim 1, wherein the alkali agent (a) is potassium hydroxide or potassium carbonate.

5. An air cleaning filter according to claim 1, wherein the oxidizing agent (c) is a combination of active manganese dioxide resulting from potassium permanganate and potassium iodate.

6. An air cleaning filter according to claim 1, wherein the air cleaning filter has a weight in the range of 50–800 g/m$^2$.

7. An air cleaning filter as in claim 1, wherein both surfaces of the web are covered with the nonwoven fabric.

8. An air cleaning filter as in claim 1, wherein an antibacterial agent is admixed with the chemical agent.

9. An air cleaning filter as in claim 1, which contains 5–15 wt. % water based on the total weight of the filter.

10. An air cleaning filter as in claim 1, wherein the web also contains an inorganic particulate selected from the group consisting of oxides, hydroxides, silicates or phosphates of Ca, Mg, Al, Fe, Zn, Ti, Zr, or Cu, of activated carbon or aluminosilicates.

* * * * *